(12) United States Patent
Pickering et al.

(10) Patent No.: US 7,363,778 B2
(45) Date of Patent: Apr. 29, 2008

(54) SEAMLESS THREE-DIMENSIONAL TOE SECTION FOR PROSTHETIC SOCKS AND PROSTHETIC SHRINKERS

(75) Inventors: John Pickering, New Hope, PA (US); Jennifer Roberts, Agency, MO (US); Jeffrey C. Dalbey, Leawood, KS (US)

(73) Assignee: Knit-Rite, Inc., Kansas City, KS (US)

( * ) Notice: Subject to any disclaimer, the term of this patent is extended or adjusted under 35 U.S.C. 154(b) by 100 days.

(21) Appl. No.: 11/457,138

(22) Filed: Jul. 12, 2006

(65) Prior Publication Data

US 2007/0043450 A1   Feb. 22, 2007

Related U.S. Application Data

(60) Provisional application No. 60/708,748, filed on Aug. 16, 2005.

(51) Int. Cl.
*D04B 1/26* (2006.01)
(52) U.S. Cl. .................. 66/178 A; 66/189
(58) Field of Classification Search .......... 66/178 R, 66/183–188, 178 A, 189; 2/239
See application file for complete search history.

(56) References Cited

U.S. PATENT DOCUMENTS

| | | | | |
|---|---|---|---|---|
| 1,983,914 A | * | 12/1934 | McCann | 66/70 |
| 3,451,232 A | * | 6/1969 | Belzidsky | 66/171 |
| 3,855,677 A | * | 12/1974 | Belzidsky | 66/170 |
| 3,991,424 A | * | 11/1976 | Prahl | 602/61 |
| 4,840,635 A | | 6/1989 | Smith et al. | |
| 5,737,943 A | * | 4/1998 | Bernhardt | 66/178 R |
| 6,158,253 A | | 12/2000 | Svoboda et al. | |

OTHER PUBLICATIONS

Wonseok, Choi, et al. "Three Dimensional Seamless Garment Knitting on V-Bed Flat Knitting Machines," Journal of Textile and Apparel Technology and Management, vol. 4, Issue 3 (Spring 2005).

* cited by examiner

*Primary Examiner*—Danny Worrell
(74) *Attorney, Agent, or Firm*—Hovey Williams LLP

(57) ABSTRACT

A stretchable fabric sleeve is configured for use as a prosthetic shrinker or as a prosthetic sock and broadly comprises a unitary receptacle broadly including a tubular section and a rounded end section. In particular, the rounded end section includes opposite panels that are knitted in seriatim with a plurality of interlaced short rows that provide a progressive taper from the open margin of the tubular section to the lowermost toe end of the end section. The progressive taper of the knitted panels permits the outermost edge of the rounded end section to assume a rounded shape that comfortably conforms to an amputated limb and is devoid of any sewn seams that would otherwise irritate the sensitive end of the amputated limb.

46 Claims, 4 Drawing Sheets

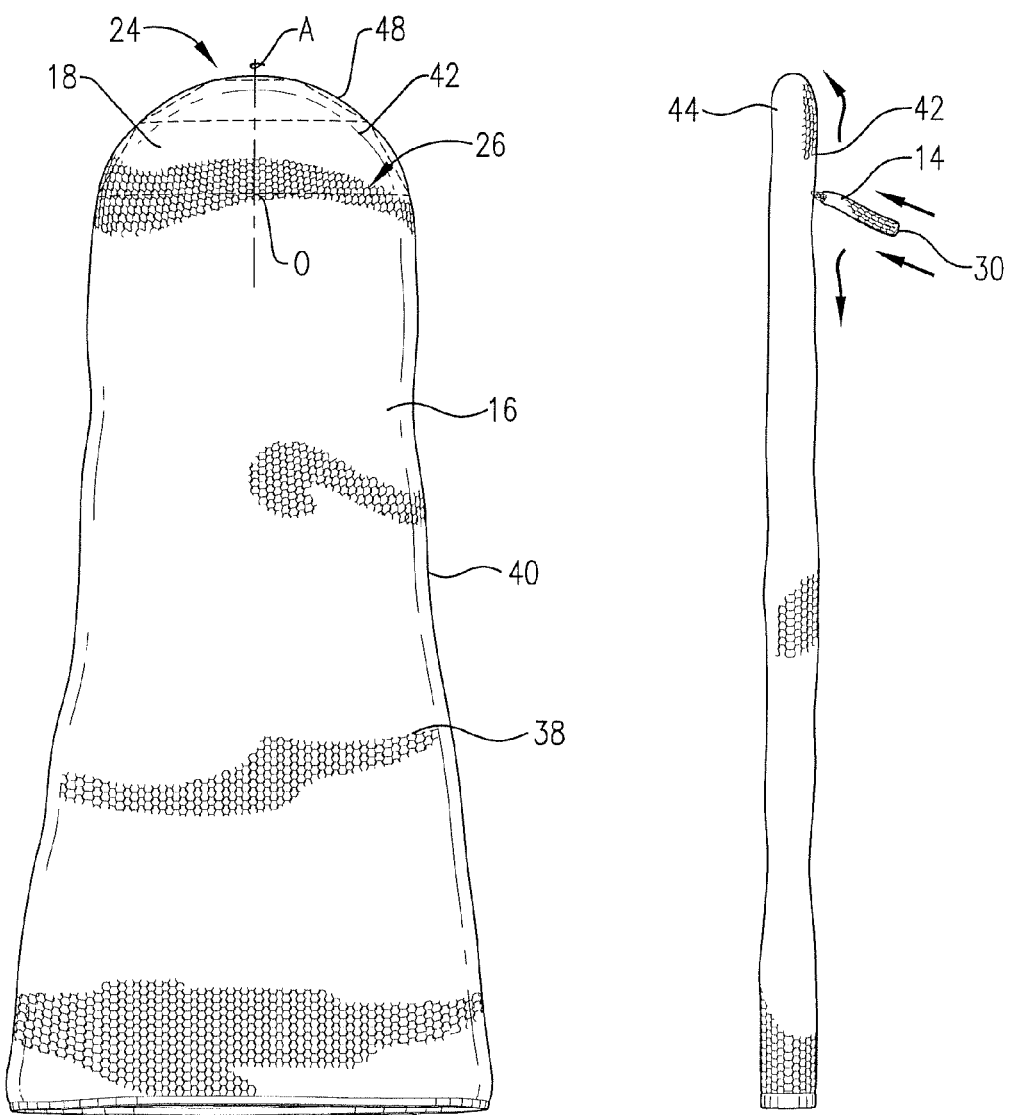
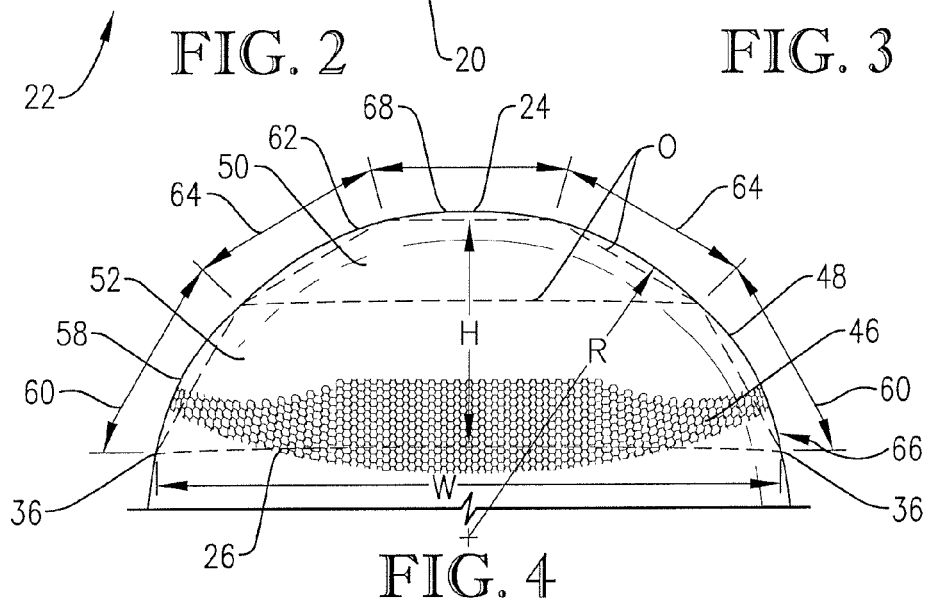
FIG. 2  FIG. 3
FIG. 4

SEAMLESS THREE-DIMENSIONAL TOE SECTION FOR PROSTHETIC SOCKS AND PROSTHETIC SHRINKERS

RELATED APPLICATION

This application claims priority of U.S. Provisional Application Ser. No. 60/708,748, filed Aug. 16, 2005, entitled SEAMLESS THREE-DIMENSIONAL TOE SECTION FOR PROSTHETIC SOCKS AND PROSTHETIC SHRINKERS, which is hereby incorporated by reference herein.

BACKGROUND OF THE INVENTION

1. Field of the Invention

The present invention relates generally to elongated fabric coverings for amputated limbs. In particular, embodiments of the present invention concern a seamlessly knitted sleeve in the form of a sock, wherein the sleeve includes a closed end with a rounded shape.

2. Discussion of Prior Art

Seamlessly knitted socks for use as a foot covering are known in the art and provide added comfort for the wearer by eliminating points where focal pressure would otherwise occur due to sewn seams. It is also known in the art to use fabric coverings over amputated limbs. For example, compressive fabric sleeves, sometimes referred to as shrinkers or prosthetic socks are worn by amputees following an amputation procedure. In one application, such sleeves are principally worn to reduce the occurrence of edema near the amputated end of the limb and to help shape the limb following surgery. In another application, these sleeves are principally worn to protect and cushion the amputated end of the limb when a prothesis is being worn adjacent to the amputated end.

Prior art shrinkers and prosthetic socks are problematic and suffer from various undesirable limitations. For instance, these prior art sleeves include a closed end for covering the amputated end of the limb. The closed end of these prior art sleeves include fabric sections, referred to as ears, of increased thickness caused by creation of the closed end. These thick sections of fabric are problematic and tend to irritate and otherwise cause focal pressure along the sensitive amputated end. Another problem associated with prior art sleeves is that the closed end is unevenly formed across its width and, therefore, tends to unevenly compress and/or cover the amputated end.

SUMMARY OF THE INVENTION

The present invention provides a compressive fabric sleeve that does not suffer from the problems and limitations of the prior art sleeves set forth above.

A first aspect of the present invention concerns a stretchable sleeve operable to be received on and conform to an amputated limb presenting a distal-most end. The stretchable sleeve broadly includes, among other things, a seamless fabric receptacle operable to receive the limb. The receptacle presents an upper open end, through which the limb is operable to be extended, and a lower toe end. The receptacle includes a tubular section projecting from the upper end, with the tubular section presenting a lowermost open margin and knitting edge locations diametrically opposed from one another across the open margin. The receptacle further includes a rounded section extending between the toe end and the lowermost open margin. The rounded section includes opposite panels joined along a common knitted edge extending from the knitting edge locations of the tubular section. The common knitted edge presents arcuate segments having a common radius that is substantially constant along the segments, wherein the rounded section is configured to receive and conform to the distal-most end of the limb.

A second aspect of the present invention concerns a stretchable sleeve operable to be received on and conform to an amputated limb presenting a distal-most end. The stretchable sleeve broadly includes, among other things, a seamless fabric receptacle operable to receive the limb. The receptacle presents an upper open end, through which the limb is operable to be extended, and a lower toe end. The receptacle includes a tubular section projecting from the upper end, with the tubular section presenting a lowermost open margin and knitting edge locations diametrically opposed from one another across the open margin. The receptacle further includes a rounded section extending between the toe end and the lowermost open margin. The rounded section includes opposite panels joined along a common knitted edge extending from the knitting edge locations of the tubular section. The panels each are defined by a plurality of interlaced stitching rows, with the number of stitches in the rows progressively decreasing from the lowermost open margin to the toe end. Each of the panels presents a first portion having a first rate of stitching decrease and a second portion having a second rate of stitching decrease, with the second rate of stitching decrease being greater than the first rate of stitching decrease.

A third aspect of the present invention concerns a stretchable sleeve operable to be received on and conform to an amputated limb presenting a distal-most end. The stretchable sleeve broadly includes, among other things, a seamless fabric receptacle operable to receive the limb. The receptacle presents an upper open end, through which the limb is operable to be extended, and a lower toe end. The receptacle includes a tubular section projecting from the upper end, with the tubular section presenting a lowermost open margin and knitting edge locations diametrically opposed from one another across the open margin. The receptacle further includes a rounded section extending between the toe end and the lowermost open margin. The rounded section includes opposite panels joined along a common knitted edge extending from the knitting edge locations of the tubular section. The common knitted edge includes a lowermost edge segment at the lower toe end of the receptacle, with the lowermost edge segment presenting a first diametrical dimension. The knitting edge locations present a second diametrical dimension, with a ratio of the first diametrical dimension to the second diametrical dimension being about $12/62$ to about $1/3$.

A fourth aspect of the present invention concerns a stretchable sleeve operable to be received on and conform to an amputated limb presenting a distal-most end. The stretchable sleeve broadly includes, among other things, a seamless fabric receptacle operable to receive the limb. The receptacle presents an upper open end, through which the limb is operable to be extended, and a lower toe end. The receptacle includes a tubular section projecting from the upper end, with the tubular section presenting a lowermost open margin and knitting edge locations diametrically opposed from one another across the open margin. The receptacle further includes a rounded section extending between the toe end and the lowermost open margin. The rounded section includes opposite panels joined along a common knitted edge extending from the knitting edge locations of the tubular section. The panels each are defined by a plurality of interlaced stitching rows, with the number of stitches in the rows progressively decreasing from the lowermost open margin to the toe end. The stitching rows present a number of short rows in which the stitches are less than an adjacent upwardly spaced row. Each of the short rows presents a tuck stitch along the knitted edge.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 2 is a front elevational view of the sleeve shown in FIG. 1, showing a tubular section and a rounded end section enclosing one end of the tubular section;

FIG. 3 is a side elevational view of the sleeve shown in FIGS. 1 and 2, showing setup and waste material prior to removal from the sleeve;

FIG. 4 is a fragmentary front elevational view of the sleeve shown in FIGS. 1-3, showing the rounded end section;

Figure 1:
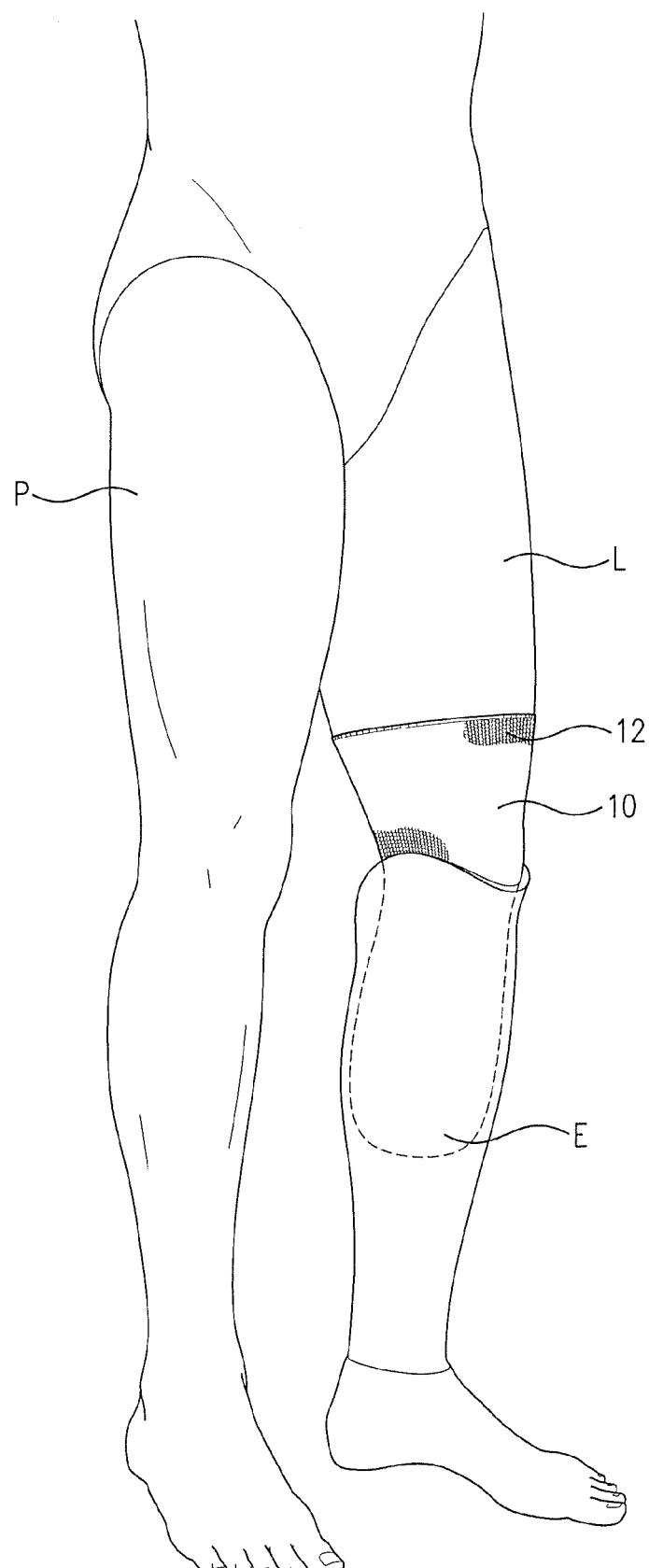
FIG. 1 is a perspective view of a compressive fabric sleeve constructed in accordance with a preferred embodiment of the present invention and fitted onto an amputee.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Turning initially to FIGS. 1-3 a compressive fabric sleeve 10 is fitted onto an amputated leg L of patient P. As will be discussed, the sleeve 10 comprises a receptacle 12 with a sock-type shape and is configured to fit snugly around the leg L and an amputated end E of the leg L. In particular, the receptacle 12 is configured to be either a prosthetic shrinker and/or sock. Thus, the inventive receptacle 12 is operable to compress the leg L to reduce the occurrence of edema and to help shape the limb following surgery. As shown in the illustrated embodiment, the receptacle 12 is also, or alternatively, operable to protect and cushion the amputated end E when a prosthetic attachment P is being worn adjacent to the amputated end E. Those of ordinary skill in the art will appreciate that the principles of the present invention are equally applicable to sleeves 10 used with another limb, such as an arm (not shown). The receptacle 12 broadly includes a setup section 14, a tubular section 16, a rounded end section 18, and a termination section 20.

The receptacle 12 is preferably knitted on a V-bed flat knitting machine (not shown). One such machine is available as Model No. SES-234S from Shima Seiki Manufacturing, Ltd. of Wakayama, Japan. However, the principles of the present invention are applicable where other machines are used to knit the inventive sleeve 10. For example, other suitable machines for knitting the sleeve 10 are Shima Seiki Model Nos. SES-124S and SES-122S. Additionally, the sleeve 10 may possibly be manufactured by knitting machines other than flatbed knitting machines, although the use of flatbed knitting machines is customary for knitting fabric articles similar to the illustrated sleeve 10 embodiment.

It will be appreciated that a standard flatbed knitting machine includes two oppositely inclined flat beds, front and rear, of needles and a yarn carrier or feeder that moves back and forth across the beds to feed yarn to the needles. The needles are shiftable along their respective longitudinal axes to ascend and descend during knitting operations. The machine is particularly well suited for knitting fabric comprising interlacing courses of yarn, with each course typically extending entirely around the knitted article. For example, all of the needles of both beds may be activated so that yarn is fed to and knitted by each of the needles, whereby a tubular, seamless article is formed by courses of plain knit, as will be described. However, certain ones of the needles, including an entire bed, may be deactivated to vary the stitching pattern of the knitted article. In fact, the above-referenced flatbed knitting machines are programmable to facilitate such activation and deactivation of the needles.

Turning to FIGS. 2 and 3, the receptacle 12 presents an upper open end 22 and a lower toe end 24. As will be discussed in greater detail, the tubular section 16 presents a lowermost open margin 26 spaced oppositely from the upper open end 22. The tubular section 16 and rounded end section 18 are joined adjacent the lowermost open margin 26 along a phantom line O.

Figure 5:
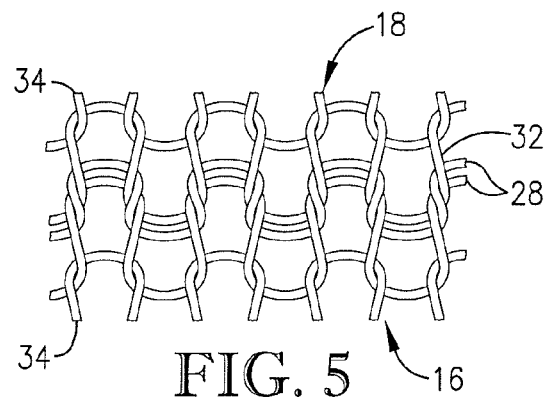
FIG. 5 is a fragmentary plan view of the setup courses shown in FIG. 3, showing a double-stranded, 1×1 rib knit closure.

Turning to FIGS. 2 and 5, the setup section 14 extends toward the lowermost open margin 26 and includes a setup course 28 and a waste material portion 30. The waste material portion 30 is the first part of the sleeve 10 to be knitted and enables separation between sleeves 10 as multiple sleeves 10 are manufactured in seriatim. The waste material portion 30 is removable from the setup course 28 and the rest of the sleeve 10.

The setup course 28 provides a double-stranded, 1×1 rib knit closure 32 from which the remaining portion of the sleeve 10 may be formed. That is, once the closure 32 is formed, courses 34 of the tubular and rounded end sections 16,18 may thereafter be knitted to lock in the setup course 28, with the setup course 18 serving to close the sleeve 10. The setup course 28 may be visually perceptible, but is quite minuscule and adds negligible thickness to the sleeve 10. In addition, the setup course 28 is predominately on the outside of the sleeve 10 so as to provide maximum comfort to the wearer. As shown in FIG. 5, subsequent courses 34 located below the setup course 28 are part of the rounded end section 18, while the upper subsequent courses 34 are part of the tubular section 16. Additional preferred features of the setup course 28 are disclosed in U.S. Pat. No. 6,158,253, issued Dec. 12, 2000, entitled SEAMLESS, FORM FITTING FOOT SOCK, which is hereby incorporated by reference herein.

The setup section 14, tubular section 16, and rounded end section 18 preferably include courses 34 of a weft-knitted, 1×1 rib fabric. However, the principles of the present invention are equally applicable where the receptacle 12, including the tubular section 14, includes other types of weft-knitted rib fabrics. Furthermore, the sections 14,16,18 are preferably formed of a standard "plain knitting pattern" or "jersey knit" and with a yarn configuration, defined herein, as being either a 1-ply configuration (also referred to as light-weight) wherein knitting is done with one strand, a 3-ply configuration wherein two strands are used, or a 5-ply configuration wherein three strands are used.

Most preferably, the sections 14,16,18 are knitted with two oppositely twisted corespun high-stretch yarn strands (e.g., in what is referred to as a 3-ply fabric). However, it is entirely within the ambit of the present invention to knit with other yarns that are not corespun. Furthermore, it is also within the ambit of the present invention to knit with a yarn incorporating one or more various materials such as wool, nylon, cotton, acrylic, polyester, or spandex. Additional materials suitable for use in embodiments of the present invention are further disclosed in the above-incorporated U.S. patent. Most preferably, the corespun yarn includes acrylic and lycra.

It is believed that corespun yarn greatly enhances the form fitting nature of the receptacle 12. The present invention involves combining multiple corespun strands to form the yarn used in knitting the sections 14,16,18, such that the torsional biases of the strands are canceled. This may be accomplished a number of ways. In the preferred embodiment, two oppositely twisted strands (referred to as "Z-twist" and "S-twist" strands) are combined so that their oppositely directed torsional biases cancel one another out. Typically, the oppositely twisted strands are simultaneously routed to the knitting machine carrier from respective sources and the strands simply cling to one another (i.e., they are not otherwise positively attached or adhered to one another before knitting). Alternatively, it is possible to use a plied corespun yarn, wherein two or more similarly twisted strands (e.g., two Z-twist strands) are twisted about one another in an opposite direction (e.g., in the "S" direction when the two Z-twist strands are combined). Additional features of the preferred corespun yarn are disclosed in the above-incorporated U.S. patent.

Turning to FIGS. 2 and 4, the tubular section 16 is a knitted tube extending from the upper open end 22 to the lowermost open margin 26. The lowermost open margin 16 includes diametrically-opposed knitting edge locations 36, as will be discussed further. The tubular section 16 is formed by knitted courses 34 as discussed above, including front and back half-courses 38 or rows, that are built up to form the tubular structure along a receptacle axis A. In the illustrated embodiment, the tubular section 16 includes a generally straight tapered edge 40 along which the front and back rows 38 are joined. The illustrated taper, as is common for shrinkers and prosthetic socks, is tapered from the upper open end 22 to the lowermost open margin 26 by about 50-60%. For example, where the tubular section 16 is about 12 inches long, and the end 22 is about 6 inches wide, the lowermost open margin 16 is about 4 inches wide. However, it is within the ambit of the present invention for the tubular section 16 to have an untapered edge or to have a curved tapered edge. The edge 40 is formed by introducing a widening fashioning stitch within at least some of the courses 34. In other words, the tubular section 16 is fashioned to include the tapered edge 40. Additional features of other similar preferred fashioning courses are depicted in the above-incorporated U.S. patent.

Turning to FIGS. 3 and 4, the rounded end section 18 is a knitted cap that extends from the lowermost open margin 26 to the lower toe end 24. In other words, the end section 18 effectively caps the lowermost open margin 26 of the receptacle 12 and is preferably knitted so that the receptacle 12 is unitary. In the preferred embodiment, the cap completely encloses the lowermost open margin 26. However, as will be shown in a subsequent embodiment, the principles of the present invention are applicable where the end section 18 does not completely enclose the lowermost open margin 26. The end section 18 is formed by front and back panels 42,44 that are knitted together to form the unitary end section 18 and are knitted so as to be positioned in registry with each other. As will be discussed in greater detail, the panels 42,44 are formed separately by knitting successive carriage rows 46 (also referred to as stitching rows), rather than full courses.

The carriage rows 46 of each panel 42,44 are knitted to form a rounded tapered edge 48 of the end section 18. In particular, the carriage rows 46 are selectively short-rowed to form a gradually inward taper from the diametrically-opposed knitting edge locations 36 of the lowermost open margin 26 to the lower toe end 24. In other words, a successive row 46 includes one or more additional or fewer stitches than the previous row 46. Preferably, such widening occurs with every row 46 of the particular panel 42,44. However, the principles of the present invention are applicable where widening (or narrowing) occurs only with selected rows 46. The illustrated carriage rows 46 of one of the panels 42,44 are preferably positioned in registry with corresponding carriage rows 46 of the other of the panels 42,44. In this manner, the rounded tapered edge 48 preferably assumes a uniform shape with substantially constant curvature.

Figure 6:
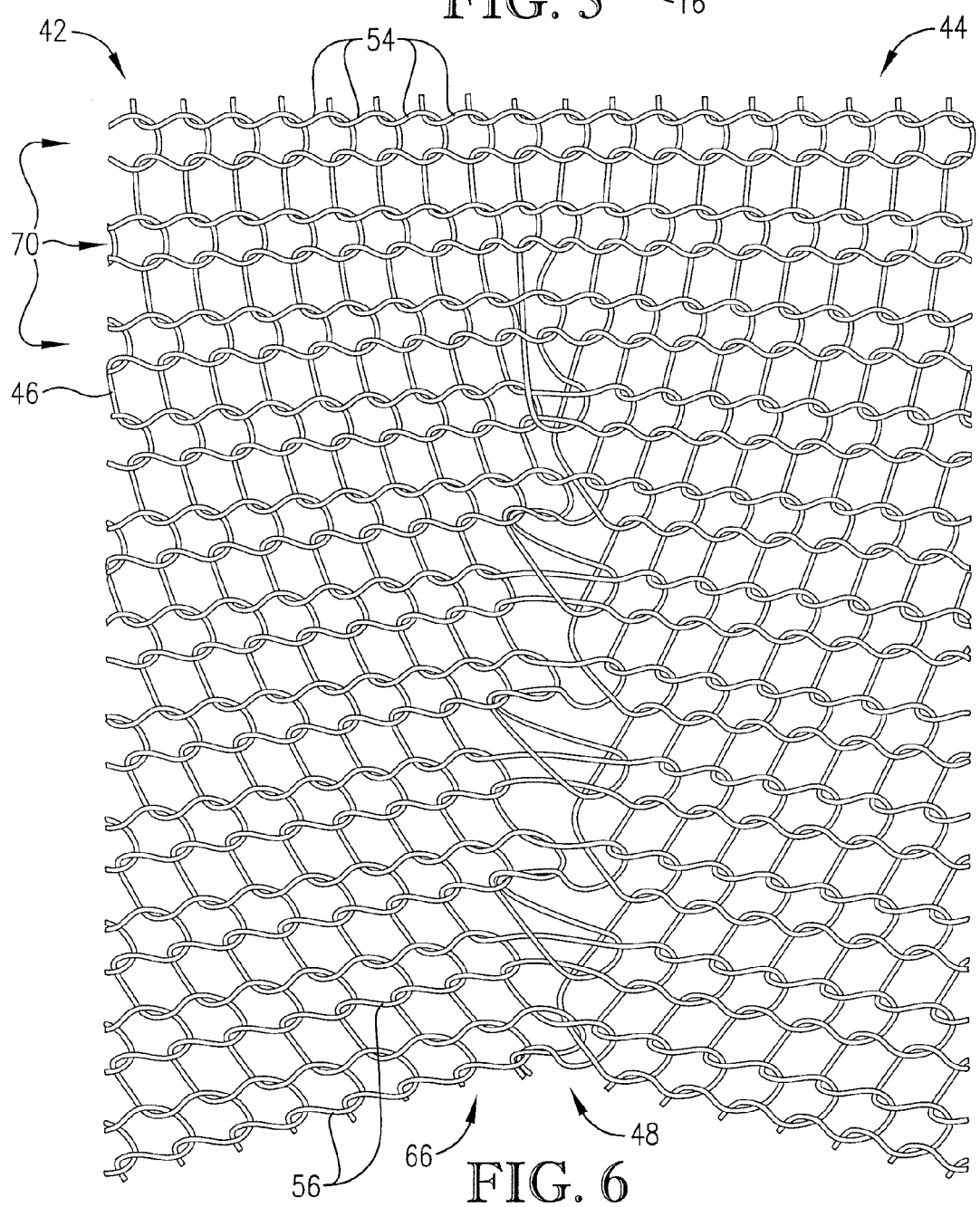
FIG. 6 is a fragmentary plan view of the rounded end section shown in FIGS. 1 and 2, showing front and back short-row panels knitted together.
Figure 7:
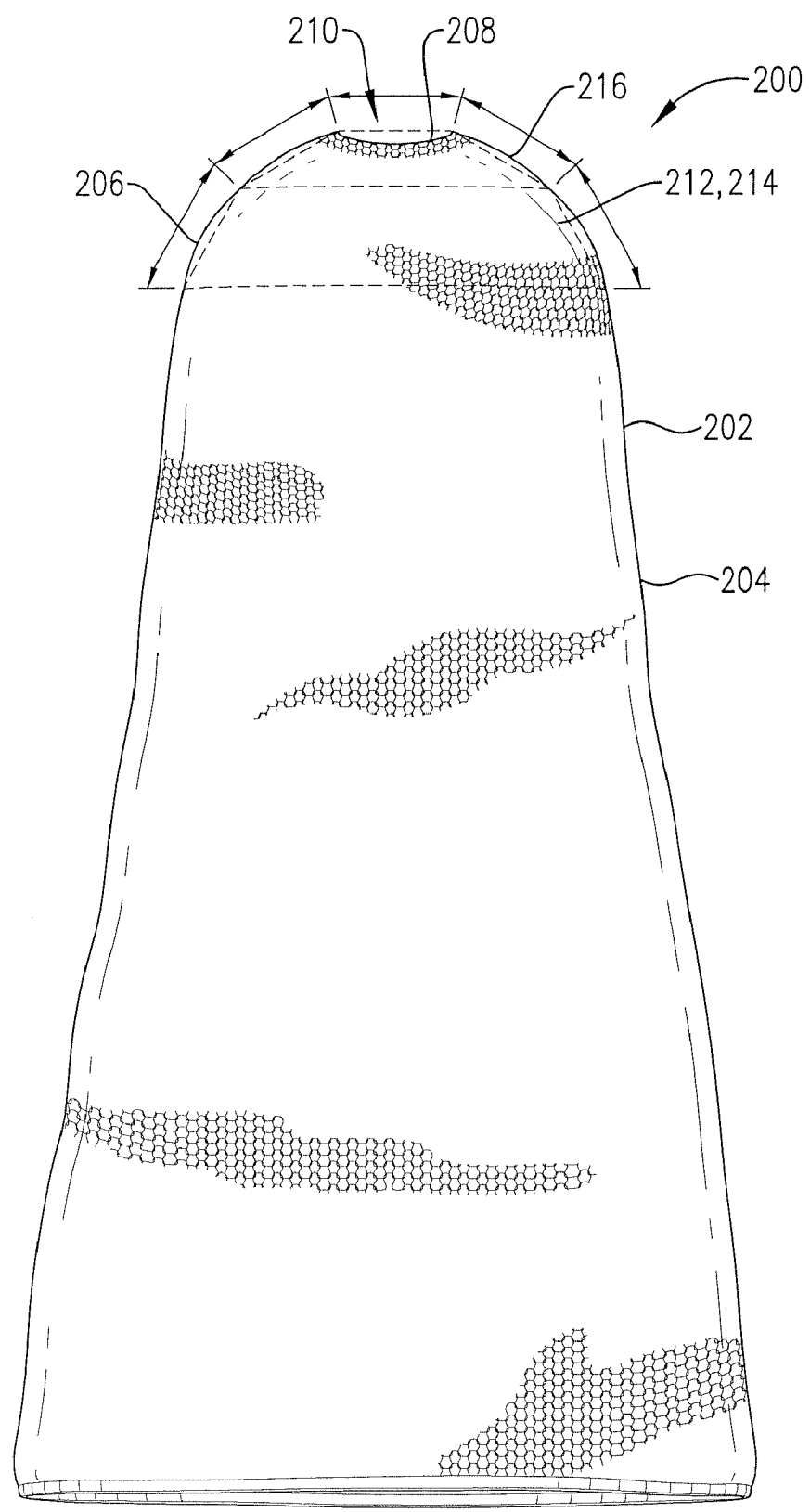
FIG. 7 is an elevational view of a compressive fabric sleeve constructed in accordance with an alternative embodiment of the present invention, where the sleeve includes a tubular section and a rounded end section with an opening therein.

Turning to FIGS. 4 and 6, each of the panels 42,44 preferably includes lower and upper short-row portions 50,52. In the illustrated embodiment, the upper short-row portion 52 is adjacent the lowermost open margin 26 and the lower short-row portion 50 is adjacent the lower toe end 24. The portions 50,52 are integrally knitted to form the respective unitary panel 42,44. Each of the short-row portions 50,52 includes a plurality of short rows 54, wherein each short row 54 includes a number of stitches 56 less than the adjacent upwardly spaced row 54. In this manner, a series of adjacent short rows 54 cooperatively form a shaped edge. As shown particularly in FIG. 4, phantom line O schematically illustrates an outline of the pattern of short rows 54 that forms the portions 50,52 with distinctly tapered sides.

For example, the upper short-row portions 52 preferably includes short rows 54 that taper along an upper arcuate tapered edge segment 58 at a first rate of stitching decrease 60 (the taper shown schematically in phantom line O) toward the lower toe end 24. The lower short-row portion 50 preferably includes short rows 54 that taper along a lower arcuate tapered edge segment 62 at a second rate of stitching decrease 64 (the taper shown schematically in phantom line O) toward the lower toe end 24. While the illustrated portions 50,52 include different rates of stitching decrease, the principals of the present invention are applicable where the panels 42,44 may include panel portions where at least some of the portions have the same rate of stitching decrease.

Turning to FIG. 4, the panels 42,44 are preferably tapered to form the edge 48 in a substantially rounded shape with a substantially constant radius R between sides of the panels 42,44, as will be discussed in greater detail. In particular, it has been discovered that the uniquely rounded shape of the lower toe end 24 is preferably achieved by the formation of edge 48 with more than one taper along each side of the panels 42,44, and, more preferably, with two distinct tapers in series (i.e., with two straight-edged knitting patterns therebetween). It has also been discovered that the elasticity of the weft-knitted fabric construction along with the elasticity of the corespun yarn particularly enables the distinct knit tapers 60,64 of the short row portions 50,52 to shift and stretch relative to each other in order to naturally assume the arcuate shape of the edge 48. In other words, even with the relatively straight taper of the knitting pattern, the end section 18 assumes a very arcuate shape. However, the principles of the present invention are applicable where the edge 48 includes more than two distinct tapers along each side of the panels 42,44.

Turning to FIG. 6, each of the stitching rows 46 comprising the upper panel portion 52 preferably includes a tuck stitch 66 spaced at one end thereof along the edge 48. More preferably, tuck stitch 66 is spaced on opposite ends of adjacent rows 46 such that the tuck stitches 66 are knitted on alternating sides of the upper panel portion 52 with successive rows 46. Each of the stitching rows 46 comprising the lower panel portion 50 include two tuck stitches 66 spaced at one end thereof. Again, the tuck stitches 66 are knitted on alternating sides of the lower panel portion 50 along the edge 48 and with successive rows 46. However, the principles of the present invention are equally applicable where at least some of the rows 46 are devoid of tuck stitches 66.

The edge 48 further includes a lowermost edge segment 68 along the lower toe end 24. This segment 68 is substantially untapered and perpendicular to the receptacle axis A. The segment 68 is defined by an area where vertical wales 70 extend continuously therethrough between the panels 42,44. In comparison, respective wales 70 from each panel 42,44 are knitted together along the tapered edge segments 58,62 but do not extend between the panels 42,44 to form a continuous wale 70. The segment 68 also is devoid of tuck stitching 66, where the tapered edge segments 58,62 preferably include tuck stitching 66 as discussed above. Most notably, the segment 68 preferably includes a narrow width that enables the edge 48 to assume its uniquely rounded shape. As discussed above, the elasticity of the knitted construction and of the yarn permits the stitches around the lowermost edge segment 68 to stretch and otherwise shift relative to each other. In this manner, even the lowermost edge segment 68 is able to assume an arcuate form, with the entire edge 48 being continuously curved between the edge locations 36.

The illustrated receptacle 12 is preferably knitted in a range of sizes to accommodate and conform to variously sized limbs. Furthermore, the rounded end section 18 itself is preferably knitted in a range of sizes so as to accommodate and conform to those various limbs. For example, it has been determined that three distinct receptacle sizes, as will be described, are preferable: narrow, regular, and wide. However, it is within the ambit of the present invention to have other sizes, as will be discussed. Furthermore, it has been determined that three different types of fabric are preferable to provide a range of sleeve thickness: 1-ply (also referred to as light-weight), 3-ply, and 5-ply. However, it is consistent with the principles of the present invention where sleeve thickness ranges from 1-ply up to 8-ply. Thus, these variations in sleeve size and material thickness require different short-row configurations in order to provide a substantially rounded end geometry. In particular, the number of carriage rows in each panel portion and the number of needles removed from each row are adjusted based on the overall width of the end section 18 and material thickness.

Table 1 illustrates the preferred number of stitches along the edge segment 68 including front and back panels 42,44 (identified in Table 1 as "Narrowest, A") and along the lowermost open margin 26 including front and back panels 42,44 (identified in Table 1 as "Widest, B") for each corresponding size of sleeve 10 and each material thickness. For example, the regular size sleeve 10 with 3-ply yarn material thickness preferably includes about twenty (20) stitches along the edge segment 68 and tapers outwardly to the lowermost open margin 26 to about sixty-two (62) stitches. In other words, the ratio of widths of the edge segment 68 to the lowermost open margin 26 is about one-third (⅓). Furthermore, the panels 42,44 each include the upper panel portion 52 comprising about seven (7) carriage rows 46 and the lower panel portion 50 including about nine (9) carriage rows 46.

Furthermore, the number of stitches removed for each carriage row 46 in the corresponding portions 50,52 are also illustrated in Table 1. For example, in the "narrow" sleeve size with 1-ply fabric identified in Table 1, the upper panel portion 52 (identified in Table 1 as "1st panel portion") is configured so that one needle is removed for each carriage row 46, and the lower panel portion 50 (identified in Table 1 as 2nd panel portion") is configured so that two needles are removed for each carriage row 46. In this manner, the rates of stitching decrease 60,62 are determined.

TABLE 1

| Size: Narrow Total Needles Narrowest, A | Widest, B | Ratio A/B (%) | End Width | End Height |
|---|---|---|---|---|
| 1-Ply | 12 | 62 | 19.4% | 2 ½" | ¾" |
| 1st panel portion | 1 Needle/CR; 7 CRs (1 × 7) | | | | |
| 2nd panel portion | 2 × 9 | | | | |
| 3-Ply | 16 | 52 | 30.8% | 2 ¾" | ¾" |
| 1st panel portion | 1 × 6 | | | | |
| 2nd panel portion | 2 × 6 | | | | |
| 5-Ply | 12 | 36 | 33.3% | 3" | ¾" |
| 1st panel portion | 1 × 4 | | | | |
| 2nd panel portion | 2 × 4 | | | | |

| Size: Regular Total Needles Narrowest, A | Widest, B | Ratio A/B (%) | End Width | End Height |
|---|---|---|---|---|
| 1-Ply | 20 | 84 | 23.8% | 3 ½" | 1" |
| 1st panel portion | 1 × 10 | | | | |
| 2nd panel portion | 2 × 11 | | | | |
| 3-Ply | 20 | 62 | 32.3% | 3 ¾" | 1" |
| 1st panel portion | 1 × 7 | | | | |
| 2nd panel portion | 2 × 7 | | | | |
| 5-Ply | 14 | 46 | 30.4% | 3 ¾" | 1" |
| 1st panel portion | 1 × 6 | | | | |
| 2nd panel portion | 2 × 5 | | | | |

TABLE 1-continued

| | Size: Wide Total Needles Narrowest, A | Widest, B | Ratio A/B (%) | End Width | End Height |
|---|---|---|---|---|---|
| 1-Ply | 26 | 108 | 24.1% | 4 ½" | 1 ¼" |
| 1st panel portion | 1 × 15 | | | | |
| 2nd panel portion | 2 × 13 | | | | |
| 3-Ply | 24 | 88 | 27.3% | 4 ¾" | 1 ¼" |
| 1st panel portion | 1 × 12 | | | | |
| 2nd panel portion | 2 × 10 | | | | |
| 5-Ply | 16 | 62 | 25.8% | 5" | 1 ¼" |
| 1st panel portion | 1 × 9 | | | | |
| 2nd panel portion | 2 × 7 | | | | |

Turning to FIG. 4, the shape of the rounded end section 18 can be further described by a width dimension W (identified in Table 1 as "End Width") adjacent the lowermost open margin 26 and a height dimension H (identified in Table 1 as "End Height") between the lowermost open margin 26 and the lower toe end 24. Table 1 illustrates the actual dimensions of the rounded end section 18 for the various sleeve sizes and yarn constructions discussed above. Notably, a ratio of the height dimension H to the width dimension W ranges from about 3/10 to about ¼ based on the values provided in Table 1. As discussed, additional sizes of sleeve 10 are within the scope of the present invention. For example, a "child size" having a width dimension W of about 2 inches and an "extra wide size" having a width dimension W of about 7 inches (with the end height for these alternative sleeves preferably being dimensioned relative to the width W according to the range noted above) are consistent with the principles of the present invention.

Turning to the manufacture of the illustrated receptacle 12, knitting is preferably done on a V-bed flat knitting machine as discussed above. The preferred knitting machines preferably provide either "seven cut" "ten cut," or "twelve cut" needle configurations where each bed has seven, ten, or twelve needles per inch, respectively. Furthermore, the "seven cut," "ten cut," and "twelve cut" beds are used, respectively, with the 5-ply, 3-ply, and 1-ply fabric constructions.

Turning to FIG. 3, the knitting process preferably begins in the usual manner with the carrier of the knitting machine providing yarn alternatively to each of the needles on the front and rear beds to form the waste material portion 30 of the setup section 14 in the direction shown by the arrows. Once the waste material portion 30 is formed, the setup course 28 is knitted on front and rear beds (again, as shown by the arrows) and the end section 18 is ready to be knitted.

The end section 18 is preferably formed by only one of the beds of the knitting machine. The needles of the other bed are consequently deactivated but still hold onto the setup course 28. The needles at the opposite ends of the activated bed are gradually deactivated (e.g., one or two needles after every course), with each deactivated needle descending to no longer accept yarn from the carrier but still holding onto whatever yarn has been fed thereto before it descends. This causes the stitching rows to narrow. Once the remaining activated needles present a width corresponding to the relatively narrow lower toe end 24, the deactivated needles will be gradually reactivated in a reverse manner to widen the courses. In view of the foregoing, the front panel 40 is knitted while the needles are gradually deactivated, while the rear panel 42 is formed as the needles gradually reactivate.

Once all of the needles have been reactivated, the knitting bed will have the same needles activated as those used to create the setup course 28. At this point, both beds of the knitting machine are activated and formation of the tubular section 16 is commenced. It may therefore be said that the illustrated tubular section 16 begins at the first full course 34 (i.e., at the course just above the rounded end section 18). It is particularly noted that the tubular section 22 presents a tubular shape that tapers, as discussed above.

Once the tubular section 16 is finished, the termination section 20 is knit adjacent the upper open end 22. The termination section 20 of the receptacle 12 is preferably knit in the same manner as the tubular section 16. However, the termination section 20 is preferably formed of yarn that is capable of fusing the stitching at the upper open end 22 of the receptacle 12 so that unraveling of the fabric may be avoided without requiring traditional sewing techniques (i.e., without requiring a seam). In the preferred embodiment, the termination section 20 is knitted from a heat fusing yarn such as that available under the designation "PORTE" from Nitto Boseki Co., Ltd. of Japan. The sleeve 10 is preferably washed in hot water before it is packaged to cause the PORTE brand yarn to fuse and seal the top of the sleeve 10. Again, this fusing of the yarn in the termination section 20 will prevent fraying and unraveling of the unsewn upper end 22 of the receptacle 12.

FIG. 6 illustrates an alternative embodiment of the present invention. For the purpose of brevity, primarily the differences of the alternative embodiment from the preferred embodiment will be described. In FIG. 6, an alternative compressive fabric sleeve 200 includes an alternative receptacle 202 with a tubular section 204 and an alternative rounded end section 206.

The rounded end section 206 is knitted to present an opening 208 therein at the lower toe end 210. In particular, the rounded end section 206 includes panels 212,214 similar to the preferred embodiment. The panels 212,214 include a plurality of short rows that are knitted to form an edge 216. The edge 216 defines the opening 208 extending along the lower toe end 210. The opening 208 is preferably configured to receive a portion of a prosthesis (not shown) therethrough. Furthermore, the end section 206 includes an interlocking stitch (not shown) that defines the edge 216 as it extends around the opening 208. As is customary, the interlocking stitch is interlaced with adjacent short row stitches and thereby prevents unraveling of the end section 206 adjacent the opening 208.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A stretchable sleeve operable to be received on and conform to an amputated limb presenting a distal-most end, said stretchable sleeve comprising:
a seamless fabric receptacle operable to receive the limb,
said receptacle presenting an upper open end, through which the limb is operable to be extended, and a lower toe end,
said receptacle including a tubular section projecting from the upper end, with said tubular section presenting a lowermost open margin and knitting edge locations diametrically opposed from one another across the open margin,
said receptacle further including a rounded section extending between the toe end and the lowermost open margin,
said rounded section including opposite panels joined along a common knitted edge extending from the knitting edge locations of the tubular section,
said common knitted edge presenting arcuate segments having a common radius that is substantially constant along the segments, wherein the rounded section is configured to receive and conform to the distal-most end of the limb.

2. The stretchable sleeve as claimed in claim 1,
said common knitted edge presenting a lowermost edge segment spaced between the arcuate segments at the lower toe end.

3. The stretchable sleeve as claimed in claim 2,
said panels including a plurality of interlaced wales, a central number of which are spaced along and project from the lowermost edge segment,
said central number of wales being devoid of tuck stitching adjacent the lowermost edge segment.

4. The stretchable sleeve as claimed in claim 1,
said panels presenting a maximum panel height,
said lowermost open margin presenting a width defined between the knitting edge locations,
said radius being dimensioned so that a ratio of the maximum panel height to the lower open end width ranges from about $3/10$ to about $1/4$.

5. The stretchable sleeve as claimed in claim 4,
said radius being dimensioned so that the ratio of the maximum panel height to the lower open end width is about $1/4$.

6. The stretchable sleeve as claimed in claim 1,
said common knitted edge circumscribing an angle less than 180 degrees.

7. The stretchable sleeve as claimed in claim 1,
said receptacle comprising weft-knitted, 1×1 rib fabric.

8. The stretchable sleeve as claimed in claim 7,
said fabric being knitted of a corespun yarn.

9. The stretchable sleeve as claimed in claim 8,
said corespun yarn including multiple strands, at least two of which are oppositely twisted.

10. The stretchable sleeve as claimed in claim 8,
said corespun yarn comprising acrylic and lycra.

11. The stretchable sleeve as claimed in claim 1,
said panels each being defined by a plurality of interlaced stitching rows, with the number of stitches in the rows progressively decreasing from the lowermost open margin to the toe end,
each of said panels presenting a first portion having a first rate of stitching decrease and a second portion having a second rate of stitching decrease, with the second rate of stitching decrease being greater than the first rate of stitching decrease.

12. The stretchable sleeve as claimed in claim 1,
said common knitted edge including a lowermost edge segment at the lower toe end of the receptacle, with said lowermost edge segment presenting a first diametrical dimension,
said knitting edge locations presenting a second diametrical dimension, with a ratio of the first diametrical dimension to the second diametrical dimension being about $12/62$ to about $1/3$.

13. The stretchable sleeve as claimed in claim 1,
said panels each being defined by a plurality of interlaced stitching rows, with the number of stitches in the rows progressively decreasing from the lowermost open margin to the toe end,
said stitching rows presenting a number of short rows in which the stitches are less than an adjacent upwardly spaced row,
each of said short rows presenting a tuck stitch along the knitted edge.

14. A stretchable sleeve operable to be received on and conform to an amputated limb presenting a distal-most end, said stretchable sleeve comprising:
a seamless fabric receptacle operable to receive the limb,
said receptacle presenting an upper open end, through which the limb is operable to be extended, and a lower toe end,
said receptacle including a tubular section projecting from the upper end, with said tubular section presenting a lowermost open margin and knitting edge locations diametrically opposed from one another across the lowermost open margin,
said receptacle further including a rounded section extending between the toe end and the lowermost open margin,
said rounded section including opposite panels joined along a common knitted edge extending from the knitting edge locations of the tubular section,
said panels each being defined by a plurality of interlaced stitching rows, with the number of stitches in the rows progressively decreasing from the lowermost open margin to the toe end,
each of said panels presenting a first portion having a first rate of stitching decrease and a second portion having a second rate of stitching decrease, with the second rate of stitching decrease being greater than the first rate of stitching decrease.

15. The stretchable sleeve as claimed in claim 14,
said panels being substantially similarly knitted, such that the interlaced stitching rows of each panel is in registry with corresponding interlaced stitching rows of the other panel.

16. The stretchable sleeve as claimed in claim 14,
said stitching rows presenting a number of short rows in which the stitches are less than an adjacent upwardly spaced row,
said first rate of stitching decrease being defined by each of said short rows in the first portion having one stitch fewer than the adjacent upwardly spaced row.

17. The stretchable sleeve as claimed in claim 16,
said second rate of stitching decrease being defined by each of said short rows in the second portion having two stitches fewer than the adjacent upwardly spaced row.

18. The stretchable sleeve as claimed in claim 14,
said first portion being adjacent the lowermost open margin, and said second portion being adjacent the lower toe end.

19. The stretchable sleeve as claimed in claim 14, substantially all of said stitching rows being short rows in which the stitches are less than an adjacent upwardly spaced row.

20. The stretchable sleeve as claimed in claim 14, said receptacle comprising weft-knitted, 1×1 rib fabric.

21. The stretchable sleeve as claimed in claim 20, said fabric comprising a corespun yarn.

22. The stretchable sleeve as claimed in claim 21, said corespun yarn including multiple strands, at least two of which are oppositely twisted.

23. The stretchable sleeve as claimed in claim 21, said corespun yarn comprising acrylic and lycra.

24. The stretchable sleeve as claimed in claim 14, said common knitted edge including a lowermost edge segment at the lower toe end of the receptacle, with said lowermost edge segment presenting a first diametrical dimension,
said knitting edge locations presenting a second diametrical dimension, with a ratio of the first diametrical dimension to the second diametrical dimension being about 12/62 to about 1/3.

25. The stretchable sleeve as claimed in claim 14, said stitching rows presenting a number of short rows in which the stitches are less than an adjacent upwardly spaced row,
each of said short rows presenting a tuck stitch along the knitted edge.

26. A stretchable sleeve operable to be received on and conform to an amputated limb presenting a distal-most end, said stretchable sleeve comprising:
a seamless fabric receptacle operable to receive the limb,
said receptacle presenting an upper open end, through which the limb is operable to be extended, and a lower toe end,
said receptacle including a tubular section projecting from the upper end, with said tubular section presenting a lowermost open margin and knitting edge locations diametrically opposed from one another across the open margin,
said receptacle further including a rounded section extending between the toe end and the lowermost open margin,
said rounded section including opposite panels joined along a common knitted edge extending diametrically from the knitting edge locations of the tubular section,
said common knitted edge including a lowermost edge segment at the lower toe end of the receptacle, with said lowermost edge segment presenting a first diametrical dimension,
said knitting edge locations presenting a second diametrical dimension, with a ratio of the first diametrical dimension to the second diametrical dimension being about 12/62 to about 1/3.

27. The stretchable sleeve as claimed in claim 26, said lowermost edge segment being substantially untapered.

28. The stretchable sleeve as claimed in claim 27, said common knitted edge presenting arcuate segments, said arcuate segments extending from opposite ends of the lowermost edge segment.

29. The stretchable sleeve as claimed in claim 27, said untapered lowermost edge segment presenting an opening.

30. The stretchable sleeve as claimed in claim 26, said ratio of the first diametrical dimension to the second diametrical dimension being about one-fifth.

31. The stretchable sleeve as claimed in claim 26, said receptacle comprising weft-knitted, 1×1 rib fabric.

32. The stretchable sleeve as claimed in claim 31, said fabric comprising a corespun yarn.

33. The stretchable sleeve as claimed in claim 32, said corespun yarn including multiple strands, at least two of which are oppositely twisted.

34. The stretchable sleeve as claimed in claim 32, said corespun yarn comprising acrylic and lycra.

35. The stretchable sleeve as claimed in claim 26, said panels each being defined by a plurality of interlaced stitching rows, with the number of stitches in the rows progressively decreasing from the lowermost open margin to the toe end,
said stitching rows presenting a number of short rows in which the stitches are less than an adjacent upwardly spaced row,
each of said short rows presenting a tuck stitch along the knitted edge.

36. A stretchable sleeve operable to be received on and conform to an amputated limb presenting a distal-most end, said stretchable sleeve comprising:
a seamless fabric receptacle operable to receive the limb,
said receptacle presenting an upper open end, through which the limb is operable to be extended, and a lower toe end,
said receptacle including a tubular section projecting from the upper end, with said tubular section presenting a lowermost open margin and knitting edge locations diametrically opposed from one another across the lowermost open margin,
said receptacle further including a rounded section extending between the toe end and the lowermost open margin,
said rounded section including opposite panels joined along a common knitted edge extending from the knitting edge locations of the tubular section,
said panels each being defined by a plurality of interlaced stitching rows, with the number of stitches in the rows progressively decreasing from the lowermost open margin to the toe end,
said stitching rows presenting a number of short rows in which the stitches are less than an adjacent upwardly spaced row,
each of said short rows presenting a tuck stitch along the knitted edge.

37. The stretchable sleeve as claimed in claim 36, said common knitted edge presenting arcuate segments.

38. The stretchable sleeve as claimed in claim 37, said tuck stitch being positioned along one of the corresponding arcuate segments.

39. The stretchable sleeve as claimed in claim 37, substantially all of said stitching rows being short rows.

40. The stretchable sleeve as claimed in claim 37, said interlaced stitching rows of one of said panels being substantially positioned in registry with corresponding interlaced stitching rows of the other of said panels.

41. The stretchable sleeve as claimed in claim 36, said tuck stitches being on alternating ends of adjacent carriage rows.

42. The stretchable sleeve as claimed in claim 36, said common knitted edge including a lowermost edge segment at the lower toe end,
said lowermost edge segment presenting an opening.

43. The stretchable sleeve as claimed in claim 36, said receptacle comprising weft-knitted, 1×1 rib fabric.

44. The stretchable sleeve as claimed in claim 43, said fabric comprising a corespun yarn.

45. The stretchable sleeve as claimed in claim 44, said corespun yarn including multiple strands, at least two of which are oppositely twisted.

46. The stretchable sleeve as claimed in claim 44, said corespun yarn comprising acrylic and lycra.

* * * * *